(12) United States Patent
Chang et al.

(10) Patent No.: US 9,095,599 B2
(45) Date of Patent: Aug. 4, 2015

(54) O-(SUBSTITUTED BENZYL) PHOSPHORAMIDATE COMPOUNDS AND THERAPEUTIC USE

(75) Inventors: Junbiao Chang, Zhengzhou (CN); Zheng Wang, Suzhou (CN); Suping Zhou, Philadelphia, PA (US)

(73) Assignee: Nanjing Molecular Research, Inc., Nanjing (CN)

( * ) Notice: Subject to any disclaimer, the term of this patent is extended or adjusted under 35 U.S.C. 154(b) by 0 days.

(21) Appl. No.: 13/978,272

(22) PCT Filed: Dec. 30, 2011

(86) PCT No.: PCT/US2011/068131
§ 371 (c)(1),
(2), (4) Date: Oct. 15, 2013

(87) PCT Pub. No.: WO2012/094248
PCT Pub. Date: Jul. 12, 2012

(65) Prior Publication Data
US 2014/0038916 A1     Feb. 6, 2014

Related U.S. Application Data

(60) Provisional application No. 61/460,458, filed on Jan. 3, 2011.

(51) Int. Cl.
| | | |
|---|---|---|
| *A61K 31/7076* | (2006.01) | |
| *A61K 31/706* | (2006.01) | |
| *A61K 31/7068* | (2006.01) | |
| *A61K 31/7072* | (2006.01) | |
| *A61K 45/06* | (2006.01) | |
| *C07H 19/10* | (2006.01) | |
| *C07H 19/20* | (2006.01) | |
| *C07H 19/12* | (2006.01) | |
| *A61K 31/075* | (2006.01) | |
| *C07F 9/6558* | (2006.01) | |
| *C07F 9/6561* | (2006.01) | |

(52) U.S. Cl.
CPC ............. *A61K 31/706* (2013.01); *A61K 31/075* (2013.01); *A61K 31/7068* (2013.01); *A61K 31/7072* (2013.01); *A61K 31/7076* (2013.01); *A61K 45/06* (2013.01); *C07F 9/65583* (2013.01); *C07F 9/65616* (2013.01); *C07H 19/10* (2013.01); *C07H 19/12* (2013.01); *C07H 19/20* (2013.01)

(58) Field of Classification Search
USPC ................. 514/48, 49, 51, 52; 536/26.8, 26.7
See application file for complete search history.

(56) References Cited

U.S. PATENT DOCUMENTS

| | | | |
|---|---|---|---|
| 7,071,176 | B2 | 7/2006 | Uckun et al. |
| 2006/0142238 | A1 | 6/2006 | McGuigan |
| 2009/0169504 | A1 | 7/2009 | Sommadossi |
| 2009/0215715 | A1 | 8/2009 | McGuigan et al. |
| 2009/0306007 | A1 | 12/2009 | Wagner |
| 2010/0016251 | A1 | 1/2010 | Sofia et al. |
| 2013/0210757 | A1 | 8/2013 | Huang et al. |

FOREIGN PATENT DOCUMENTS

| | | |
|---|---|---|
| WO | WO-2006063149 | 6/2006 |
| WO | WO-2009086192 | 7/2009 |
| WO | WO-2010075549 | 7/2010 |
| WO | WO-2010081082 | 7/2010 |

OTHER PUBLICATIONS

Froehler et al., "Phosphoramidate analogues of DNA: synthesis and thermal stability of heteroduplexes," Nucleic Acids Research (1988): 16(11):4831-4839.
Wolff, Manfred E., "Burger's Medicinal Chemistry, 5ed, Part 1", John Wiley & Sons, 1995, pp. 975-977.
Banker, G.S. et al., "Modern Pharmaceutics, 3ed.", Marcel Dekker, New York, 1996, p. 596.
Gardelli et al. "J. Med. Chem." (2009), vol. 52, pp. 5394-5407.

*Primary Examiner* — Kristin Vajda
(74) *Attorney, Agent, or Firm* — Fox Rothschild LLP; Wansheng Jerry Liu

(57) ABSTRACT

This application discloses novel phosphoramidate and phosphonoamidate prodrugs of nucleosides, nucleotides, C-nucleosides, C-nucleotides, phosphonates, and other alcohol-containing drugs; use of these prodrugs for treatment of infectious diseases and cancers, in particular, liver infections and cancers; and methods of preparing these novel phosphoramidate and phosphonoamidate prodrugs.

19 Claims, No Drawings

O-(SUBSTITUTED BENZYL) PHOSPHORAMIDATE COMPOUNDS AND THERAPEUTIC USE

CROSS-REFERENCE TO RELATED APPLICATIONS

This application is the 35 U.S.C. 371 National Phase Application of International Application Serial No. PCT/US2011/068131, filed on Dec. 30, 2011, which in turn claims priority under 35 U.S.C. §119(e) to U.S. Provisional Patent Application Ser. No. 61/460,458, filed on Jan. 3, 2011, both of which are hereby incorporated by reference in their entirety.

FIELD OF THE INVENTION

The present invention relates to O-(substituted benzyl) phosphoramidate prodrugs and their therapeutic use.

BACKGROUND OF THE INVENTION

Nucleoside analogues have been developed as antiviral and anticancer agents. Nucleotide kinases phosphorylate nucleosides to their corresponding 5'-monophophates which are further converted into their di- and tri-phosphates by cellular nucleotide kinases.

It is now known that some nucleosides are weakly active simply because they cannot be efficiently phosphorylated by kinases or are not substrates of kinases at all, as evidenced by that some inactive nucleosides, when converted chemically to triphosphates, become potently active against certain viruses in vitro. Nucleoside phosphates (nucleotides) per se cannot be used as drugs often because they are de-phosphorylated by membrane nucleotides and/or other hydrolases before entering the cells or are too polar to enter the cells. To improve biological activity of nucleosides, their phosphate prodrugs have been intensively studied because they can potentially bypass the rate-limiting first step of phosphorylation. Recently, phosphoramidate prodrug approach has been proved to be an effective method to convert biologically inactive nucleosides to active nucleoside mono-phosphate bypassing the rate-limiting first step of phosphorylation (J. Med. Chem., 50 (22), 5463-5470, 2007). Nucleoside phosphoramidate has been reported to efficiently deliver nucleoside 5'-monophosphate into liver (WO 2008/121634; WO 2008/082601 and WO 2008/082602). In recent years, there are a number of patent applications disclosing utilization of the phosphoramidates as prodrugs to deliver nucleoside monophosphates to tissues, in particular to the liver (U.S. Pat. No. 6,455,513, WO 2009/052050, WO 2008/121634, WO 2008/0833101, WO 2008/062206, WO 2007/002931, WO 2008/085508, WO 2007/095269, WO 2006/012078, WO 2006/100439). The nucleoside monophosphates can be further phosphorylated to di-, and then biologically active triphosphate.

However, the above-mentioned phosphoramidate approaches based on McGuigan's technology (U.S. Pat. No. 6,455,513) have various limitations due to potential neurotoxicity and liver and kidney damages caused by phenol released from prodrugs (Carcinogenesis 1993, 14: 2477-2486; Mutat. Res. 1991, 249, 1: 201-209).

Mcguigan's phosphoramidate of nucleoside usually can demonstrate maximum biological activity in cell line assays because it can release nucleoside or nucleotide quickly in the cells. It was reported that phosphoramidate prodrug of d4T could not be detected in plasma after oral administration (Drug Metab. Dispos. 2001, 29, 1035). Phosphoramidate is stable in gastric fluid and may be absorbed in the stomach. On the other hand, phosphoramidate may decompose readily in intestinal fluid to ala-d4T-MP. This metabolite may be absorbed in the intestine and further metabolized to yield nucleoside d4T. Another possibility is that this metabolite (ala-d4T-MP) may not be absorbed efficiently in intestine due to its polar nature. Therefore, bioavailability of this type of esterase sensitive phosphoramidate prodrugs is relatively low probably due to its hydrolysis catalyzed by esterase. For example, bioavailability of GS-7340, an isopropylalanyl monoamidate phenyl monoester of tenofovir, was 17% in male beagle dogs (Gilead Sciences, Antimicrob. Agents Chemother. 2005, 49, 1898).

Diamide prodrugs of nucleoside phosphonates have also been investigated, and in certain cases this approach appears to improve the potency and/or pharmacokinetic profile. However, only very limited research is available on the application of phosphoric diamides to nucleoside (anti-HIV agents, FLT, AZT; Polish J. Chem. 1993, 67, 755; Drug Design and Discovery 1995, 13, 43; Antiviral Chem. Chemother. 1992, 3, 107; 1991, 2, 35; 1995, 6, 50). PMEA diamide prodrug could not provide satisfactory bioavailability of the parent drugs probably due to its higher polarity than Tenofovir phosphonoamidate (J. Med. Chem. 2008, 51, 4331; Antimicrob. Agents Chemother. 2005, 49, 1898).

Efforts to search for phosphonate prodrugs that would be cleaved by an esterase independent mechanism have led to the discovery of two classes of prodrugs that have advanced into human clinical trials, namely bisphenyl esters and HepDirect prodrugs (J. Med. Chem. 1994, 37, 498; J. Am. Chem. Soc. 2004, 126, 5154; J. Pharmacol. Exp. Ther. 2005, 312, 554). Bisbenzyl esters have also been investigated but the simple unsubstituted benzyl ester is cleaved too slowly to be of use as a prodrug (Bioorg. Med. Chem. Lett. 2007, 17, 3412). Erion et al disclosed that cyclic phosphate or phosphonate prodrugs which are stable in the presence of esterase can enhance liver specific drug delivery (Erion, M et al U.S. Pat. No. 7,303,739 and reference thereof). Erion's prodrugs are activated by P450 in the liver. However, clinical application of this approach may be limited by potentially adverse side effects caused by aromatic metabolites, and the efficiency of releasing bioactive phosphate or phosphonate is rather dubious.

Recently, bis[(para-methoxy)benzyl]phosphonate prodrug was reported to have improved stability and enhanced cell penetration (Bioorg. Med. Chem. Lett. 2007, 17, 3412). However, no further details were presented. Since it is known that simple benzyl phosphate prodrug and O-benzyl phosphoramidate are too stable to release active nucleoside phosphate, new prodrug forms of nucleoside and nucleotide compounds are still being actively pursued.

SUMMARY OF THE INVENTION

This invention provides, in one aspect, novel prodrug forms of small molecule drug substances, in particular, nucleosides and nucleotides. Since benzyl alcohols and their oxidized metabolites, benzoic acids, are relatively non-toxic compounds, we investigated phosphate or phosphonate prodrugs having a benzyl group with such substituents (e.g. 2-methyl substitution) destabilizing the bond that attaches benzyl to phosphate or phosphonate. These prodrugs were surprisingly discovered to release substituted benzyl moiety efficiently in cells probably involving O-dealkylation mediated by cytochrome P(450) (CYP) enzymes (J. Med. Chem. 1967, 10, 861; J. Chem. Soc. Perkin Trans. 1992, 2, 1145) or other mechanisms or simply hydrolysis in a more acidic subcellular compartment.

Thus, in one aspect the present invention provides O-(substituted benzyl)phosphoramidate and phosphonoamidate prodrugs of nucleoside, nucleotide, C-nucleoside, C-nucleotide, phosphonate, and alcohol containing drug.

In one embodiment, the present invention provides a compound of formula I:

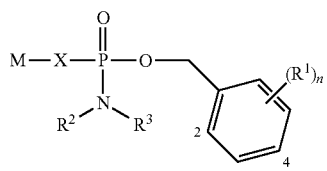

or a pharmaceutically acceptable prodrug, salt, stereoisomer, tautomer, or solvate thereof, wherein:

n is 1, 2, 3, 4, or 5;

X is oxygen (O) or —CH$_2$—;

M is a nucleoside, acyclonucleoside, C-nucleoside, or alcohol-containing drug molecule moiety;

$R^1$ at each occurrence is independently selected from acyloxy, acyl-NH—, CH$_3$, methoxy, alkyl, alkyloxyl, alkylamino, cycloalkyl, cycloalkyloxy, cycloalkylamino, aryl, aryloxy, arylamino, and arylalkyl, all optionally substituted;

$R^2$ and $R^3$ are independently selected from H, alkyl, aryl, alkynyl, alkenyl, cycloalkyl, heterocyclyl and heteroaryl, all optionally substituted, wherein the heterocyclyl and heteroaryl each comprises one to three heteroatoms independently selected from O, S, and N, or alternatively, $R^2$ and $R^3$ together, along with the N-atom to which they are attached, form an optionally substituted 4- to 7-membered ring.

In another aspect the present invention provides efficient delivery of nucleoside phosphates or phosphonates into cells, particularly into the liver target, by use of the phosphoramidate and phosphonoamidate prodrugs of the present invention. These prodrugs are resistant to esterases so that their bioavailability can be improved.

In another aspect, the present invention provides use of a compound as described herein as a prodrug of nucleoside, acyclic nucleoside, C-nucleoside, nucleotide, or other alcohol-containing drug molecule. In some embodiments, the compounds of the present invention can be used in combination with a second therapeutically active drug.

In another aspect, the present invention provides a pharmaceutical composition comprising any compound described here, and a pharmaceutically acceptable carrier or diluent.

In another aspect, the present invention provides method of treating a viral infection or cancer, comprising administration of any compound as described here, or a pharmaceutically acceptable prodrug thereof, to a patient in need of the treatment.

In another aspect, the present invention provides a method of treating a viral infection or cancer, comprising administration of a pharmaceutical composition as described here to a patient in need of the treatment.

In another aspect, the present invention provides use of any compound described herein in the manufacture of medicament for treatment of viral infections or cancers.

These and other aspects of the present invention will be better appreciated by reference to the following drawings and detailed description.

DETAILED DESCRIPTION OF THE INVENTION

The present invention relates to chemical compounds that have enhanced therapeutic potency, particularly potency with respect to cancers (such as leukaemia), viral infections (including HIV, HBV and HCV), liver disorders (including liver cancer), and metabolic diseases (such as diabetes, hyperlipidemia, atherosclerosis, and obesity).

In one aspect the present invention provides nucleoside phosphoramidate and phosphonoamidate compounds of a variety of therapeutic agents.

In one preferred embodiment of the present invention, the compound is an O-(substituted benzyl)phosphoramidate; and in another preferred embodiment, the compound is an O-(substituted benzyl)phosphonoamidate.

In certain embodiments, while not being limited to any theory, it is possible that the parent drug is mainly obtained from selective metabolism of the phosphoramidate or phosphonoamidate compound in the liver. Thus the parent drug is capable of accumulating in the liver of a host. By selectively targeting and activating compounds in the liver, potentially undesired distribution of active compound in the gastrointestinal tract can be reduced.

Some nucleosides were biologically inactive simply because they could not be phosphorylated by kinases. In certain embodiments, the prodrugs of the present invention, derivatized from these nucleosides, may become biologically active since the prodrugs directly deliver nucleoside monophosphate bypassing the rate limiting first step of phosphorylation.

Since these methods allow accumulation of the nucleoside phosphate or phosphonate compounds disclosed herein in the liver of a host, the methods described herein can be useful, for example, for treatment and/or prophylaxis of diseases or disorders of the liver, such as liver cancer, hepatitis B or C.

A method for the treatment of a liver disorder is also provided that includes administering an effective amount of a compound provided herein, either alone or in combination or alternation with another therapeutically effective agent, optionally in a pharmaceutically acceptable carrier.

Taking advantages of destabilization of bond of benzyl-OP by substituent on phenyl ring, it has been found that this kind of benzyl esters of phosphoramidates or phosphonoamidates of parent drugs can be cleaved in vivo efficiently and these phosphoramidates or phosphonoamidates are highly potent therapeutic agents which deliver parent drug directly into tissues in particular in the liver. Prodrugs with high lipophilicity of the present invention readily penetrate cell membrane so as to improve pharmacokinetics and/or bioavailabity of parent drugs. These prodrugs may be activated by P450 and/or other enzymes enriched in the liver.

Phosphoramidate and phosphonoamidate compound forms of a variety of therapeutic agents of the present invention are provided, as well as their use in the treatment of hepatitis infections (in particular hepatitis B and C viruses) and liver disorders, including cancer, malaria, and fibrosis and metabolic diseases, such as diabetes, hyperlipidemia, atherosclerosis, and obesity.

In one embodiment, the present invention provides a compound of formula I:

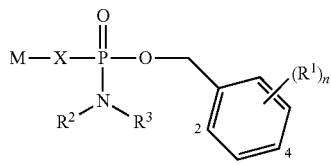

or a pharmaceutically acceptable prodrug, salt, solvate, stereoisomer, tautomer, polymorphic form, or metabolite thereof, wherein:

n is 1, 2, 3, 4, or 5;

X is oxygen (O) or —CH$_2$—;

M is a nucleoside, acyclonucleoside, C-nucleoside, or alcohol-containing drug molecule moiety;

$R^1$ at each occurrence is independently selected from acyloxy, acyl-NH—, CH$_3$, methoxy, alkyl, alkyloxyl, alkylamino, cycloalkyl, cycloalkyloxy, cycloalkylamino, aryl, aryloxy, arylamino, and arylalkyl, all optionally substituted;

$R^2$ and $R^3$ are independently selected from H, alkyl, aryl, alkynyl, alkenyl, cycloalkyl, heterocyclyl and heteroaryl, all optionally substituted, wherein the heterocyclyl and heteroaryl each comprises one to three heteroatoms independently selected from O, S, and N, or alternatively, $R^2$ and $R^3$ together, along with the N-atom to which they are attached, form an optionally substituted 4- to 7-membered ring.

M-XH is M-OH here would represent a nucleoside or acyclonucleoside, C-nucleoside or alcohol-containing compound. M-O—P(O)(OH)$_2$ represents biologically active monophosphate of nucleoside or acyclonucleoside or C-nucleoside.

M-X can be cyclic or acyclic system.

M-CH$_2$—P(O)(OH)$_2$ is a biologically active phosphonate.

In formula I, $R^1$ is a substituting group, at least one of this kind of substituents attached to phenyl ring at various position, preferably at 2 and/or 4-position(s), selected, but is not limited to, from acyloxy, acyl-NH, CH$_3$, methoxy, alkyl, alkyloxyl, alkylamino, cycloalkyl, cycloalkyloxy, cycloalkylamino, aryl, aryloxy, arylamino, arylalkyl, all optionally substituted; and $R^2$ and $R^3$ are independently selected, but are not limited to, from H, alkyl, aryl, alkynyl, alkenyl, cycloalkyl, heterocyclic or heteroaromatic group with one to three heteroatoms (such as O, S, N), all optionally substituted; or alternatively, $R^2$ and $R^3$ can form 4- to 7-membered ring, such as pyrrolidine, all optionally substituted.

In another of this aspect, at least one $R^1$ is attached to the 2- or 4-position of the phenyl ring in formula I.

In another embodiment of this aspect, $R^2$ and $R^3$ together are —(CH2)$_i$—, wherein i is 3, 4, or 5.

In another embodiment of this aspect, $R^2$ and $R^3$ together, along with the N-atom to which they are attached, form a pyrrolidinyl group.

In another embodiment of this aspect, M is a nucleoside moiety comprising a sugar group and a base group.

In another embodiment of this aspect, the sugar group is substituted or unsubstituted ribose or 2-deoxyribose, and wherein the base group is selected from substituted or unsubstituted purines and substituted or unsubstituted pyrimidines.

In another embodiment of this aspect, the base group is selected from adenine, guanine, uracil, thymine, cytosine, and derivatives thereof.

Amino and/or hydroxyl group in M-X can be optionally protected.

In another embodiment, the compound of formula I has formula II:

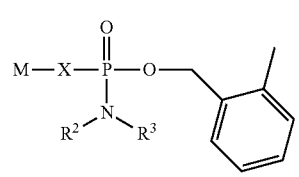

or a pharmaceutically acceptable prodrug, salt, solvate, a stereoisomic, tautomeric or polymorphic form, a metabolite thereof wherein:

$R^2$, $R^3$, X and M-XH are defined as above.

In another embodiment, the compound of formula II has formula III:

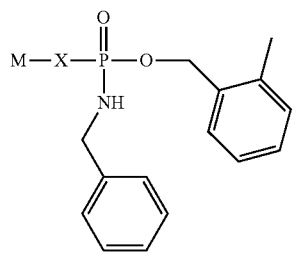

or a pharmaceutically acceptable prodrug, salt, solvate, a stereoisomic, tautomeric or polymorphic form, a metabolite thereof wherein:

X and M-X are defined as above.

In another embodiment, the compound of formula III has formula:

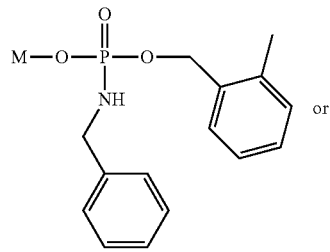

or

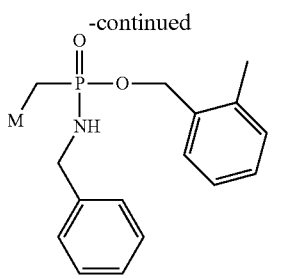

or a pharmaceutically acceptable prodrug, salt, solvate,
a stereoisomic, tautomeric or polymorphic form, a metabolite thereof
wherein: M is defined as above.

In another aspect the present invention provides use of the nucleoside phosphoramidate and phosphonoamidate compounds for the treatment of a variety of disorders, in particular, but not limited to, liver disorders. In one embodiment, the present invention provides use of a compound as described herein as a prodrug of nucleoside, acyclic nucleoside, C-nucleoside, nucleotide, or other alcohol-containing drug molecule. In some embodiments, the compounds of the present invention can be used in combination with a second therapeutically active drug.

In another aspect, the present invention provides a pharmaceutical composition comprising any compound described here, and a pharmaceutically acceptable carrier or diluent.

In another aspect, the present invention provides a method of treating viral infections, such as liver infections, or cancers, comprising administration of any compound as described here, or a pharmaceutically acceptable prodrug thereof, to a patient in need of the treatment. In some embodiments, these compounds can be used to permit high concentration of the therapeutic agent in the liver.

In another aspect, the present invention provides a method of treating a viral infection or cancer, comprising administration of a pharmaceutical composition as described here to a patient in need of the treatment.

In another aspect, the present invention provides use of any compound described herein in the manufacture of medicament for treatment of viral infections or cancers.

In another aspect the present invention provides methods for manufacture of these nucleoside phosphoramidate and phosphonoamidate compounds.

Compound of formula I can be one or a mixture of diastereomers resulted from chiral phosphorus center.

Those of skill in the art will recognize that compound of formula I can be prepared by reaction of, e.g., a hydroxyl group of said drug, for example, via condensation or dehydration.

Provided herein are also compounds, compositions and methods useful for treating hepatitis infections (HBV and HCV) and liver disorders, such as cancer, or metabolic diseases, such as diabetes, hyperlipidemia, atherosclerosis, and obesity.

DEFINITIONS

All chemical terms used herein, unless otherwise defined, take their ordinary meanings as understood by a person of skill in the art, while certain terms are defined as follows.

The term "alkyl", as used herein, includes a saturated straight, branched, or cyclic, optionally substituted hydrocarbon of typically $C_1$ to $C_{20}$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, and the like. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano and the like.

"Alkenyl" includes monovalent olefinic unsaturated hydrocarbon groups, in certain embodiment, having up to 11 carbon atoms, which can be straight-chained or branched, and having at least 1 or 2 sites of olefinic unsaturation (i.e., C═C bond). Exemplary alkenyl groups include ethenyl or vinyl (—CH═CH$_2$), allyl (—CH$_2$CH═CH$_2$), isopropenyl (—C(CH$_3$)═CH$_2$), and substituted vinyl, or the like.

"Alkynyl" includes acetylenic unsaturated hydrocarbon groups, in certain embodiments, having up to about 11 carbon atoms, which can be straight-chained or branched and having at least 1 or 2 sites of alkynyl unsaturation (i.e., CC bond). Non-limiting examples of alkynyl groups include acetylenic, ethynyl, propargyl, and the like.

The term "aryl", as used herein, includes phenyl, biphenyl, or naphthyl, and preferably phenyl. The term includes both substituted and unsubstituted moieties. The aryl group can be substituted with any described moiety, including, but not limited to, one or more moieties selected from the group consisting of halogen (fluoro, chloro, bromo or iodo), alkyl, hydroxyl, amino, alkylamino, arylamino, alkoxy, aryloxy, nitro, cyano, sulfono, sulfato, phosphono, phosphato, or phosphonoxy, either unprotected, or protected as necessary.

"Cyclic alkyl" or "cycloalkyl" includes 3-7 membered rings of hydrocarbon, such as cyclopropyl, cyclopentyl, cyclohexyl, etc., all optionally substituted.

"Heterocycles" includes 3-7 membered rings of carbon compounds with 1-3 heteroatoms, such as O, S, N in the ring, all optionally substituted.

"Heteroaromatic group" includes aromatic ring containing one to three heteroatoms, such as O, S, N, for example, pyridinyl, pyrimidinyl.

"Alkoxy or alkyloxy" includes the group —OR where R is alkyl.

"Amino" includes the radical —NH$_2$.

The term "alkylamino" or "arylamino" includes an amino group that has one or two alkyl or aryl substituents, respectively.

"Halogen" or "halo" includes chloro (Cl), bromo (Br), fluoro (F) or iodo (I).

"Monoalkylamino" includes the group alkyl-NHR'—, wherein R' is selected from alkyl or aryl.

"Thioalkyl" includes the group —SR where R is alkyl or aryl.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. In any of the structures disclosed or described herein, in particular, nucleosides or nucleotides, any hydroxyl or amino groups can be either protected or unprotected. When a hydroxyl or amino group is called to be "protected," it means that the group is protected by a removable group, such as acyl, phosphonyl, phosphate, or the like, as understood by a person of skill in the art. Suitable protecting groups for prodrugs are preferably hydrolysable under physiological conditions in vivo.

The term "nucleoside" includes natural or modified nucleoside, acyclic nucleoside and C-nucleoside.

The term "C-nucleoside" referred to nucleoside in which glycosyl bond is attached to carbon on modified nucleic bases instead of nitrogen in normal nucleoside (see reference for C-nucleoside review: Chemistry of Nucleosides and Nucleotides by Leroy B Townsend 1994, Science, Chapter 5 The Chemistry of C-nucleosides, Kyoichi A Watanabe pp 421). C-nucleoside is not limited to compound cited in the review.

"Pharmaceutically acceptable salt" includes any salt of a compound provided herein which retains its biological properties and which is not toxic or otherwise undesirable for pharmaceutical use.

The term "prodrug" as used herein refers to any compound that generates a biologically active compound when administered to a biological system as the result of spontaneous chemical reaction(s), enzyme catalyzed reactions(s), and/or metabolic process(es) or a combination of each. Standard prodrugs are formed using groups attached to functionality, e.g. —OH, —NH$_2$, associated with the drug, that cleave in vivo. The prodrugs described in the present invention are exemplary, but not limited to, and one skilled in the art could prepare other known varieties of prodrugs.

The term "L-nucleoside" refers to enantiomer of the natural and modified β-D-nucleoside analogs.

The term "arabinofuranosyl nucleoside" refers to nucleoside analogues containing an arabinofuranosyl sugar, i.e. where the 2'-hydroxyl of ribofuranosyl sugars of natural (normal) nucleoside is on the opposite face of the sugar ring.

The term "dioxolane sugar" refers to sugars that contain an oxygen atom in place of the 3' carbon of the ribofuranosyl sugar.

The term "fluorinated sugars" refers to sugars that have 1-3 fluorine atoms attached to sugar carbons.

The term "nucleoside" refers to a purine or pyrimidine base, or analogs thereof, connected to a sugar, including heterocyclic and carbocyclic analogues thereof.

The term "therapeutically effective amount" refers to an amount that has any beneficial effect in treating a disease or condition.

The term "phosphate" refers to —O—PO$_3^{2-}$.
The term "phosphoramidate" refers to —N—PO$_3^{2-}$.
The term "phosphonate" refers to —CHR—PO$_3^{2-}$.

As used herein, a "nucleoside phosphoramidate or phosphonoamidate as a therapeutic agent" includes a nucleoside (including acyclonucleoside and C-nucleoside) therapeutic agent derivatized to a phosphoramidate and phosphonoamidate having a benzyl group containing one or more substituents selected from, but not limited to, amino, $C_1$-$C_{20}$ acyloxy, $C_1$-$C_{20}$ alkyl, aryl, $C_1$-$C_{20}$ alkyloxy, aryloxy or aralkyloxy group, all optionally substituted. The therapeutic agent is, for example, an antiviral agent that includes, or has been derivatized to include, a reactive group, such as a hydroxyl, for attachment of the phosphoramidate or phosphonoamidate moiety. Such therapeutic agents include, but are not limited to, nucleosides, nucleoside analogs including acyclonucleosides, C-nucleosides, and alcohol-containing drugs. In some embodiments, phosphoramidates of nucleoside and nucleotide analogues are also provided, such as phosphoramidates of 1'-, 2'-, 3'- and 4'-branched or disubstituted nucleosides. Such compounds can be administered in a therapeutically effective amount for the treatment of infectious diseases, liver disorders, including cancers and infectious diseases, such as hepatitis B and hepatitis C infections, including resistant strains thereof.

The term "parent drug" refers to nucleosides, acyclonucleoside and their mono-phosphate drugs (M-O—PO$_3^{2-}$). The term "parent drug" also refers to phosphonate-containing drugs [R—CH$_2$—P(O)(OH)$_2$].

The term "biologically active drug or agent" refers to the chemical entity that produces the biological effect. In this invention, biologically active agents refer to nucleoside (M-OH), nucleoside mono-phosphates (M-O—PO$_3^{2-}$), nucleoside diphosphates (M-O—P$_2$O$_6^{3-}$), nucleoside triphosphates (M-O—P$_3$O$_9^{4-}$), nucleoside phosphonate [M-CH$_2$P(O)(OH)$_2$, M-CH$_2$PO$_3^{2-}$], non-nucleoside phosphonate, monophosphate (M-CH$_2$P$_2$O$_6^{3-}$) or its diphosphate (M-CH$_2$P$_3$O$_9^{4-}$), alcohol-containing compound.

The term "alkaryl" or "alkylaryl" includes an aryl group with an alkyl substituent. The term aralkyl or arylalkyl includes an alkyl group with an aryl substituent.

The term "purine" or "pyrimidine" base includes, but is not limited to, adenine, N$^6$-alkyl-6-aminopurines, N$^6$-acyl-6-aminopurines (wherein acyl is C(O)(alkyl, aryl, alkylaryl, or arylalkyl), N$^6$-benzyl-6-aminopurine, N$^6$-vinyl-6-aminopurine, N$^6$-ethynyl-6-aminopurine, 6-cycloaminopurine, 7-deazapurine, modified 7-deazapurine, thymine, cytosine, N$^4$-acylcytosine, 5-fluorocytosine, 5-methylcytosine, 6-azacytosine, uracil, 5-fluorouracil, 5-alkyluracil, 5-vinylpyrimidine, 5-ethynyluracil, 5-hydroxymethyluracil, 5-amidouracil, 5-cyanouracil, 5-iodouracil, 5-Br-vinyluracil, 5-azacytosine, 5-azauracil, triazolopyridine, imidazolopyridine, pyrrolopyrimidinyl, and pyrazolopyrimidinyl. Purine bases include, but are not limited to, guanine, adenine, 2-fluoroadenine, 2-chloroadenine, hypoxanthine, 7-deazaguanine, 7-deazaadenine, 2,6-diaminopurine, and 6-chloropurine, 6-alkoxypurine, 6-deoxyguanine, 6-alkylthiopurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" includes a group of the formula —C(O)R', wherein R' is a straight, branched, or cyclic alkyl or aryl.

The term "amino acid" includes naturally occurring and synthetic α-, β-, γ- or δ-amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

"Solvate" includes a compound provided herein or a salt thereof that further includes a stoichiometric or non-stoichiometric amount of solvent bound by non-covalent intermolecular forces. Where the solvent is water, the solvate is a hydrate.

As used herein, the term "moiety" refers to a partial structure of a molecule, often a significant portion of a molecule retaining characteristic features of the molecule. In some instances, it is exchangeable with the term "group" or "substituent." To illustrate, a "sugar moiety" means a sugar group attached to a structure of interest by a covalent bond through an oxygen atom of the sugar molecule after losing a hydrogen atom from a hydroxyl group or through a carbon atom after losing a hydroxyl group from the carbon atom.

As used herein, the terms "subject" and "patient" are used interchangeably. The terms "subject" refers to an animal, such as a mammal including a non-primate (e.g., cow, pig, horse, cat, dog, rat, and mouse) and a primate (e.g., a monkey such as a cynomolgous monkey, a chimpanzee). In one embodiment, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In one embodiment, a therapeutic agent is an agent which is known to be useful for, or has been or is currently being used for the treatment or prevention of a disorder or one or more symptoms thereof.

"Therapeutically effective amount" includes an amount of a compound or composition that, when administered to a subject for treating a disease, is sufficient to effect such treatment for the disease. A "therapeutically effective amount" can vary depending on, inter alia, the compound, the disease and its severity, and the age, weight, etc of the subject to be treated.

"Treating" or "treatment" of any disease or disorder refers, in one embodiment, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

Parent Drugs Suitable for Prodrug Derivatization of the Present Invention

Various kinds of parent drugs can benefit from the prodrug methodologies of the present invention. It is preferred that the prodrug protecting group be attached to a hydroxyl group on the parent drug. In many cases the parent drug may have many such functional groups. The preferred group selected for attachment of the prodrug is the one that is most important for biological activity and is chemically suitable for attachment to the parent drug. Thus, the phosphoric prodrug moiety will prevent the prodrug from having biological activity. An inactive prodrug should reduce systemic side effects because higher drug concentrations will be in the target organ (liver) relative to non-hepatic tissues.

There are a number of classes of therapeutically useful drugs (including nucleoside or non-nucleoside) containing hydroxyl functional group which can be used to be derivatized to phosphoramidate or phosphonoamidate prodrugs of the present invention. These compounds include nucleoside, C-nucleoside, nucleotide, phosphonate and other alcohol-containing compounds. Prodrugs disclosed herein derivatized from these compounds are considered to fall within the scope of the present invention.

Some illustrative, non-limiting examples of such compounds are described below.

One class of exemplary nucleoside drugs (D- and L-) that are therapeutically useful and can be derivatized to form prodrugs of the present invention is a compound (M-OH) of formula IV:

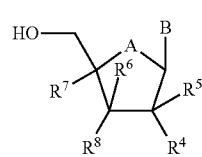

IV or pharmaceutically acceptable prodrug or metabolite thereof, wherein:

"A" is selected from, but not limited to, O, S, $CH_2$, CHF, $C=CH_2$, $C=CHF$, and $CF_2$;

$R^4$ and $R^5$ are selected independently from, but are not limited to, H, OH, $CH_3O$, F, Cl, Br, I, CN, $N_3$, methyl, ethyl, vinyl, ethynyl, chlorovinyl, fluoromethyl, difluoromethyl, and trifluoromethyl, all optionally substituted;

$R^4$ and $R^5$ can form vinyl optionally substituted with F, difluoro, Cl, Br, I, CN, and $N_3$;

$R^6$ is selected from, but is not limited to, H, methyl, ethyl, vinyl, ethynyl, chlorovinyl, fluoromethyl, difluoromethyl, and trifluoromethyl;

$R^7$ is selected from, but is not limited to, H, CN, $N_3$, methyl, ethyl, vinyl, ethynyl, chlorovinyl, fluoromethyl, difluoromethyl, and trifluoromethyl;

$R^8$ is selected from, but is not limited to, H, OH, F, cyano, and azido.

B is selected from, but is not limited to, pyrimidine and purine selected from B-1 and B-2 of formulae:

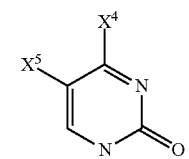

B-1

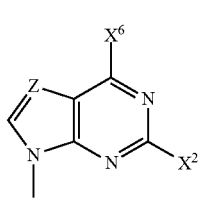

B-2 where $X^2$ is selected from H, $NH_2$, NHMe, $NMe_2$, and halogen (I, Br, Cl, F), all optionally substituted;

$X^4$ is $NH_2$ or OH;

$X^5$ is selected from, but not limited to, halogen (I, Br, Cl, F), OH, $NH_2$, methyl, vinyl, alkyl, 2-bromovinyl, and ethynyl, all optionally substituted;

$X^6$ is selected from, but not limited to, H, OH, OMe, OEt, SMe, alkyloxy, aryloxy, cyclic alkyloxy, alkylthio, arylthio, cyclic alkylthio, thienyl, furyl, alkylamino, dialkylamino, arylamino, aryl alkylamino, cyclic alkylamino, and cyclopropylamino, all optionally substituted;

Z is Nitrogen (N) or $CX^7$;

$X^7$ is selected from, but not limited to, H, vinyl, ethynyl, and halogen (I, Br, Cl, F), all optionally substituted;

Any amino and hydroxyl groups in the above structures are optionally protected.

Other modified pyrimidines or purines, such as 5-azapyrimidine, 6-azapyrimidine, 3-deazapyridine, 3-fluoro-3-deazapyrimidine, 8-aza-7-deazapurine, modified bases for C-nucleoside, or the like, are also considered to fall within the scope of the present invention.

Another class of exemplary nucleoside drugs (D- and L-) therapeutically useful and suitable to be derivatized to prodrugs of the present invention is a compound of formula V:

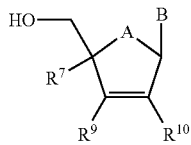

V or pharmaceutically acceptable prodrug or metabolite thereof,
wherein:
B, A, and $R^7$ are defined as above;
$R^9$ and $R^{10}$ are independently selected from, but are not limited to, H, $N_3$, F, CN, $CH_3$, alkyl, and vinyl, all optionally substituted.

Other classes of parent drugs suitable for the prodrug derivatization of the present invention include compounds of formulae (D- and L-isomers) VI and VII:

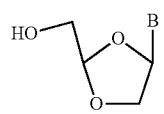

VI

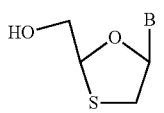

VII or pharmaceutically acceptable prodrugs or metabolites thereof,
wherein:
B is a base group defined as above.

Another class of parent drugs suitable for the prodrug modification of the present invention is selected from, but is not limited to, nucleoside phosphonates (Biochem. Pharmacol. 2007, 73, 911, which is hereby incorporated by reference).

Another class of parent drugs suitable for the prodrug derivatization of the present invention is acyclic nucleosides, including, but not limited to, acyclovir, ganciclovir and pencyclovir.

Another class of parent drug suitable for the prodrug derivatization of the present invention is C-nucleosides, a special class of nucleosides (see reference for C-nucleoside review: Chemistry of Nucleosides and Nucleotides by Leroy B Townsend 1994, Science, Chapter 5 The Chemistry of C-nucleosides, Kyoichi A Watanabe, p. 421, which is hereby incorporated by reference). C-nucleoside suitable for the present invention include, but are not limited to, the compounds cited in the review.

When some of nucleosides are not good substrates for kinases and show no biological activity while their nucleotides or nucleoside monophosphates are biologically active, the parent drugs are referred to the corresponding nucleoside monophosphates.

Preferably, compounds suitable for prodrug derivatization disclosed herein include, but are not limited to, nucleosides (including prodrugs thereof) of formulae described in Table 1:

TABLE 1

Examples of parent nucleosides

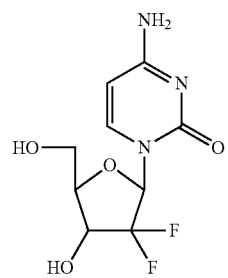 [SMILES: Nc1ccn(C2OC(CO)C(O)C2(F)F)c(=O)n1]

Gemcitabine

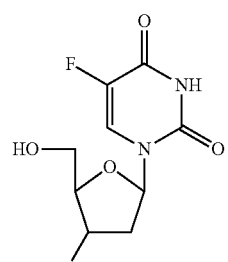

Floxuridine

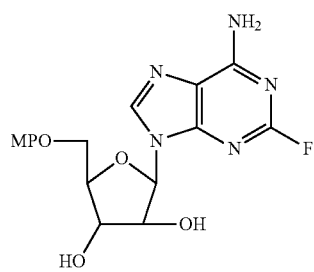

Fludarabine
MP: monophosphate

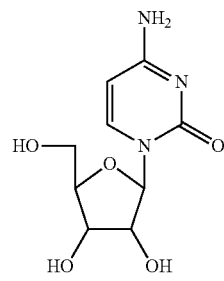 [SMILES: Nc1ccn(C2OC(CO)C(O)C2O)c(=O)n1]

Azacitidine

TABLE 1-continued
Examples of parent nucleosides
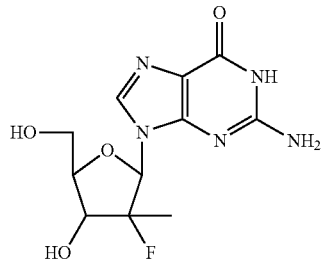 [SMILES: CC1(F)C(O)C(CO)OC1n1cnc2c(=O)[nH]c(N)nc21]
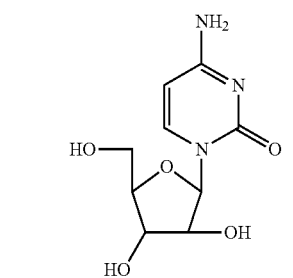 [SMILES: Nc1ccn(C2OC(CO)C(O)C2O)c(=O)n1]
Tenofovir
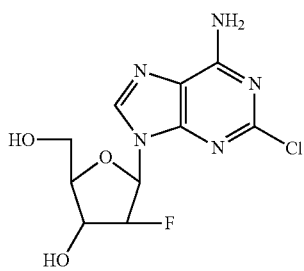 [SMILES: Nc1nc(Cl)nc2c1ncn2C1OC(CO)C(O)C1F]
Cytarabine
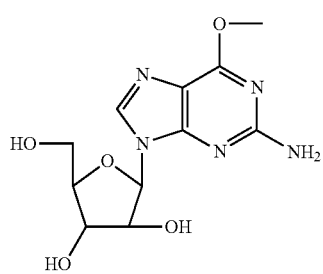 [SMILES: COc1nc(N)nc2c1ncn2C1OC(CO)C(O)C1O]
Clofarabine
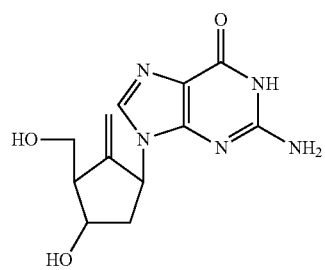 [SMILES: C=C1C(CO)C(O)CC1n1cnc2c(=O)[nH]c(N)nc21]
Nelarabine
TABLE 1-continued
Examples of parent nucleosides
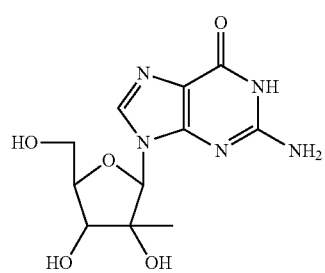 [SMILES: CC1(O)C(O)C(CO)OC1n1cnc2c(=O)[nH]c(N)nc21]
Entecavir
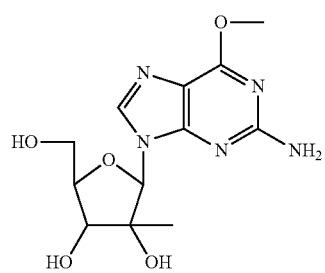 [SMILES: COc1nc(N)nc2c1ncn2C1OC(CO)C(O)C1(C)O]
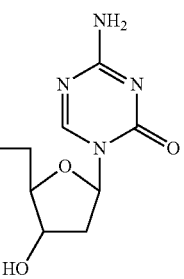
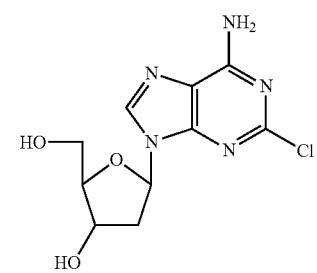 [SMILES: Nc1nc(Cl)nc2c1ncn2C1CC(O)C(CO)O1]
Decitabine
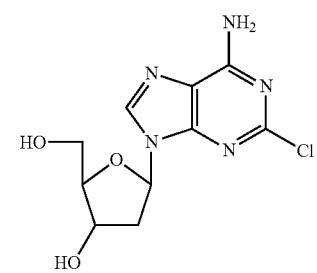 [SMILES: Nc1nc(Cl)nc2c1ncn2C1CC(O)C(CO)O1]
Cladribine

TABLE 1-continued

Examples of parent nucleosides

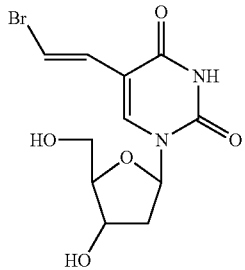

BVDU

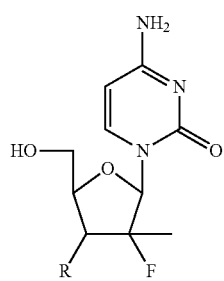

R = H, OH

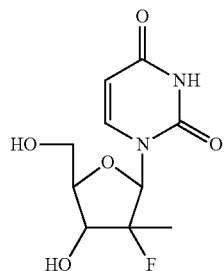 [SMILES: CC1(F)C(O)C(CO)OC1n1ccc(=O)[nH]c1=O]

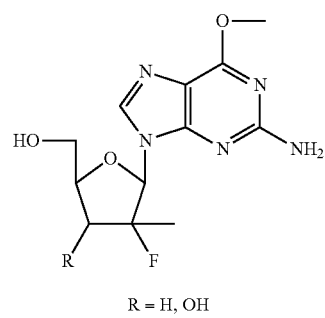

R = H, OH

Prodrugs derivatized from alcohol-containing drugs by disclosed technologies herein are also considered to fall within the scope of the present invention.

Primary hydroxyl group of nucleoside, C-nucleoside, nucleotide, C-nucleotide or other alcohol-containing compound is derivatized to phosphoramidate prodrug of the present invention. For example, Floxuridine can be derivatized to its phosphoramidate as follows:

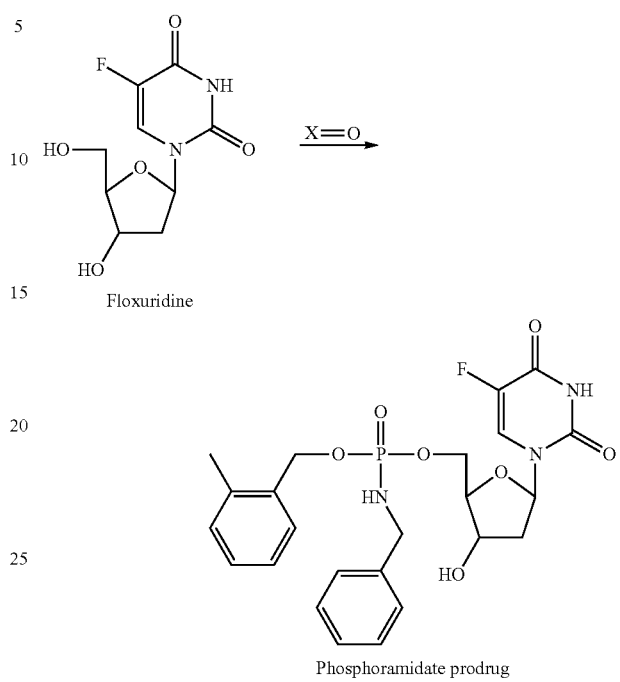

Therapeutic Use

Therapeutic use of the prodrugs herein is provided for the treatment of viral infections, cancer and other liver disorders. These prodrugs can be used to improve bioavailability and/or pharmacokinetics of parent drugs. These prodrugs and compositions disclosed herein can be administered either alone or in combination with other therapeutically effective agents.

The phosphoramidate and phosphonoamidate compounds of a variety of therapeutic agents disclosed herein can be used for the treatment of such diseases that the corresponding parent drugs are used for.

In some embodiments, prodrugs disclosed herein can also be used for the treatment of viruses resistant to parent drugs.

Such phosphoramidate and phosphonamidate compounds can advantageously have enhanced drug delivery to the liver. In some embodiments, the compounds permit delivery of an active 5'-monophosphate of a nucleoside to the liver, which can enhance the formation of active triphosphorylated compound.

In one embodiment, provided herein are methods for the treatment of liver disorders, that include the administration of an effective amount of a compound provided herein, or a pharmaceutically acceptable salt thereof to an individual host. In certain embodiments, the methods encompass the step of administering to the subject in need thereof an amount of a compound effective for the treatment of liver disorders in combination with a second agent effective for the treatment of the diseases. The compound can be any compound as described herein, and the second agent can be any second agent described in the art or herein.

Prodrug technologies of the present invention can be applied in conversion of a large number of inactive nucleosides into prodrugs of therapeutically useful nucleotides.

Thus, phosphoramidate prodrugs disclosed herein for all alcohol-containing drugs are considered to fall within the scope of the present invention.

Therapeutic use of the prodrugs herein is also provided for the treatment of hepatitis infections (including HBV and HCV) and liver disorders including liver cancer and metabolic diseases, such as diabetes, hyperlipidemia, atherosclerosis, and obesity.

Second or More Agents Useful in the Methods

In certain embodiments, the compounds and compositions provided herein are useful in methods for the treatment of a liver disorder, that comprises further administration of a second agent effective for the treatment of the disorder, such as liver cancer in a subject in need thereof. The second agent can be any agent known to those of skill in the art to be effective for the treatment of the disorder, including those currently approved by the U.S., Food and Drug Administration (FDA).

In certain embodiments, a compound provided herein is administered in combination with second agent. In further embodiments, a second agent is administered in combination with another agent. In still further embodiments, a second agent is administered in combination with two or more additional secondary agents.

Preparation of Compounds

The compounds provided herein can be prepared, isolated or obtained by any method apparent to those of skill in the art. Exemplary methods of preparation are described in detail in the Examples Section below.

Exemplary preparation of phosphoramidate of nucleoside 5-fluoro-2'-deoxyuridine (floxuridine) is illustrated in Scheme 1. Treatment of phosphorus oxychloride (1 eq. POCl$_3$) in THF with a solution of triethylamine (1 eq.) and 3-fluoro-4-methoxybenzyl alcohol (1, 1 eq.) in THF at −78° C. gives mono-ester 2, which, upon treatment with benzylamine (1 eq.) and triethylamine (1 eq.) in THF affords chlorophosphoramidate 3. Reaction of 3 with floxuridine in the presence of N-methylimidazle (NMI) produces target nucleoside phosphoramidate 4.

Scheme 1. Exemplary preparation of phosphoramidate

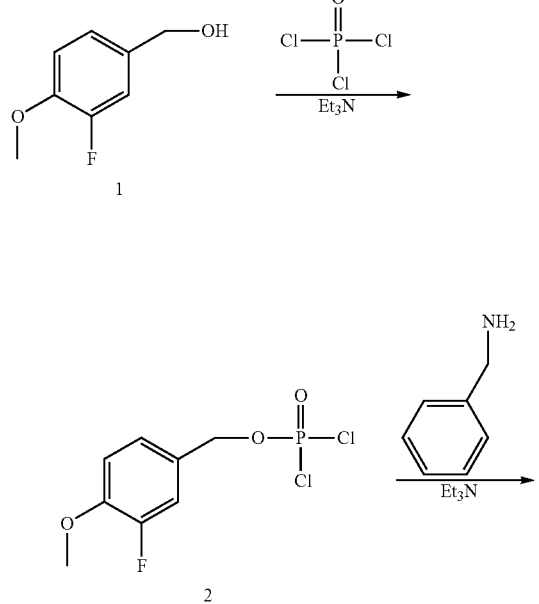

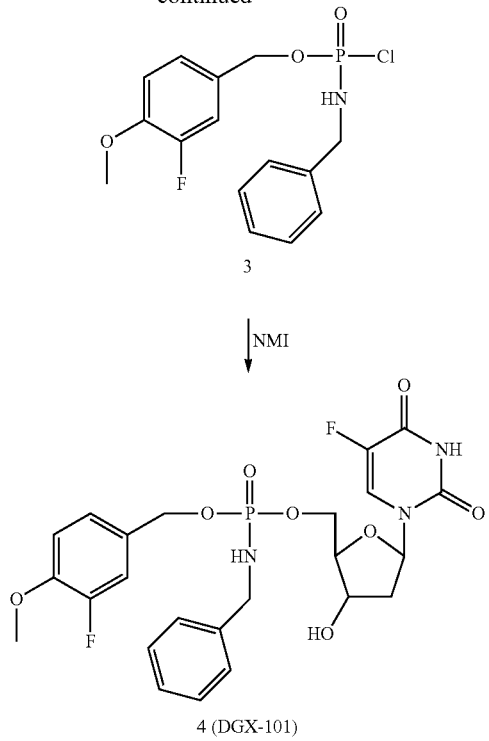

4 (DGX-101)

Scheme 1 can be applied in the general preparation of prodrugs of other alcohol-containing compounds as shown in Scheme 2.

Scheme 2. General preparation of phosphoramidate

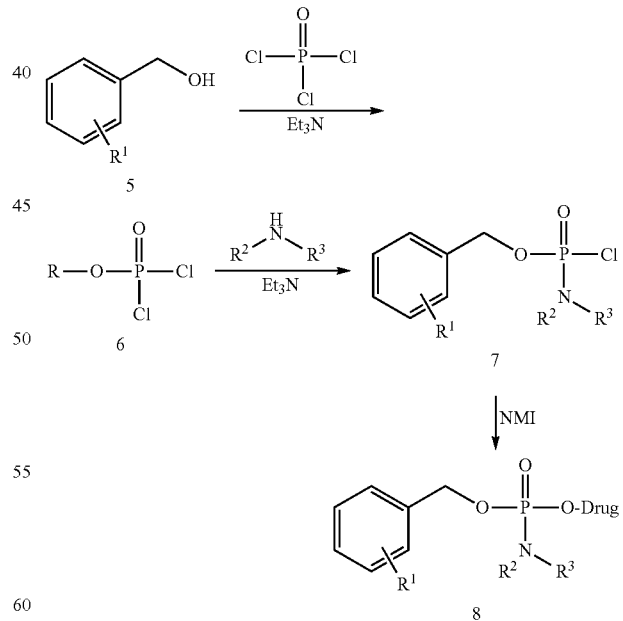

Drug-OH is a alcohol-containing drug.
$R^2$ and $R^3$ are defined as above.

For the general preparation of phosphoramidate (Scheme 2), treatment of POCl$_3$ with a solution of corresponding alcohol (5, 1 eq) and triethylamine (1 eq) gives phosphorodichloride 6. The resulting 6 is further treated with a solution of the corresponding amine (1 eq) in the presence of triethylamine (1 eq) provides chlorophosphoramidate 7. Treatment of 7 with alcohol-containing drug including nucleoside in the presence of N-methylimidazole affords phosphoramidate prodrug 8.

Biological Evaluation

1. Anticancer Activity Assay

Compounds synthesized as anti-cancer agents can be each tested in leukaemic cell lines to assess their anticancer efficacy. Th compounds can be tested using the MTS assay reagents from Promega (CellTiter96 Aqueous One solution proliferation assay). The compounds can be tested at 5 µM concentration (WO 2006/100439).

2. Anti-Hepatitis C Activity

Anti-HCV activity and cytotoxicity of compounds disclosed herein were assayed following patent method (WO 2007/027248).

3. Anti-HBV Assay

Compounds of the present invention can be assayed for anti-HBV activity according to any assay known to those of skill in the art.

4. Compounds can be assayed for accumulation of active metabolites in liver cells of a subject according to any assay known to those of skill in the art. In certain embodiments, liver cells of the subject can be used to assay for the liver accumulation of the compound or a derivative thereof, e.g. a nucleoside, nucleoside phosphate or nucleoside triphosphate derivative thereof.

5. Compounds can be assayed for accumulation of active metabolites in the liver of animals according to any assay known to those of skill in the art.

EXAMPLES

The following Examples illustrate the synthesis of representative compounds provided herein. These examples are not intended, nor are they to be construed, as limiting the scope of the claimed subject matter. It will be clear that the scope of claimed subject matter may be practiced otherwise than as particularly described herein. Numerous modifications and variations of the subject matter are possible in view of the teachings herein and, therefore, are within the scope the claimed subject matter.

Products of phosphoramidates prepared herein were mixtures of diasteromers due to the newly formed chiral center of phosphorus and tested as mixture in biological assays.

Diastereomers of prodrugs of the present invention can be separated by chromatographic methods to single isomers.

Example 1

Preparation of Phosphoramidate of Floxuridine 4
(DGX-101, See Scheme 1)

To a solution of phosphorus oxychloride (3.07 g, 20 mmol) in THF (40 mL) was added a solution of alcohol 1 (3.12 g, 20 mmol) and triethylamine (2.02 g, 20 mmol) in THF (10 mL) at −78° C. and the mixture was stirred at −78° C. for 3 h. To the resulting mixture was added a solution of benzylamine (2.14 g, 20 mmol) and triethylamine (2.02 g, 20 mmol) in THF (10 mL) at −78° C. and the mixture was stirred at −78° C. for 1 h then room temperature for overnight. THF was removed in vacuo and the residue was filtered and washed with ethyl ether (50 mL). The filtrate and washing was evaporated to give crude 3 which was dissolved in $CH_2Cl_2$ (10 mL) for the next reaction without further purification. To a suspension of nucleoside (2.42 g, 10 mml) in $CH_2Cl_2$ (40 mL) was added N-methylimidazole (5 mL) and the solution was cooled in an ice-bath. To the solution was added a solution of 3 and the resulting solution was stirred in an ice-bath for 3 h. Water (5 mL) was added and the mixture was extracted with EtOAc (2×200 mL). The organic solution was washed with 0.5 N HCl solution, aq $NaHCO_3$, brine, and dried over $Na_2SO_4$. The solvent was concentrated in vacuo and the residue was purified by silica gel chromatography (0-8% MeOH in $CH_2Cl_2$) to give compound 4 (DGX-101, 350 mg, 64%). $\delta_H$ NMR $\delta_H$ NMR (CDCL3): 7.70, 7.67 (dd, J=6.4 Hz, 1H), 6.90-7.42 (m, 8H), 6.15 (m, 1H), 4.90-5.11 (m, 2H), 3.88 (s, 3H), 3.71-4.46 (m, 6H), 1.96-2.41 (m, 2H). LC-MS (ESI): 554 [M+1]$^+$.

By following the above procedure but using corresponding nucleoside or reagent, the following prodrugs of other nucleosides can be prepared.

Example 2

DGX-102

$\delta_H$ NMR (CDCL3): 7.70, 7.67 (dd, J=6.4 Hz, 1H), 7.13-7.31 (m, 9H), 6.15 (m, 1H), 4.90-5.11 (m, 2H), 3.71-4.46 (m, 6H), 2.26, 2.25 (ss, 3H), 1.96-2.41 (m, 2H). LC-MS (ESI): 520 [M+1]$^+$.

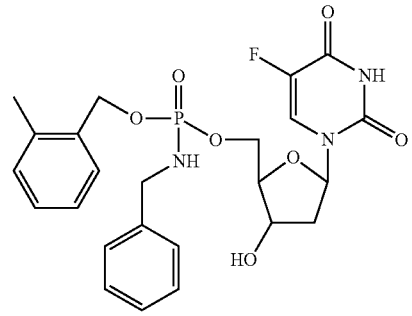

DGX-102

Example 3

DGX-104

$\delta_H$ NMR (CDCl$_3$): 8.93 (ss, 1H), 6.95-7.40 (m, 9H), 6.11 (d, 1H), 5.44 (dd, 1H), 5.00, 4.85 (m, 2H), 3.48-4.40 (m, 11H), 1.36 (dd, 3H). LC-MS (ESI) 568 [M+H]$^+$.

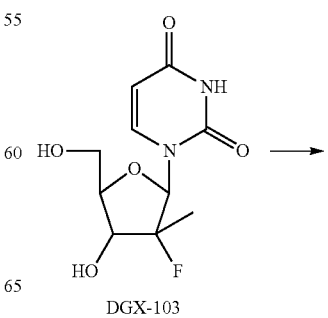

DGX-103

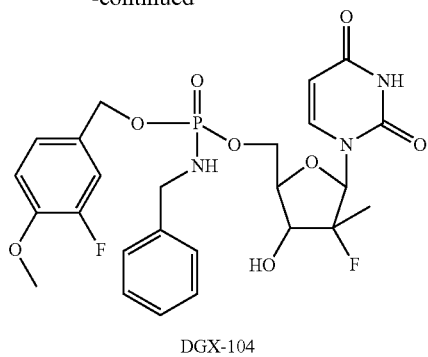

DGX-104

Example 4

DGX-105

δ$_H$ NMR (CDCl$_3$): 8.90 (br. S, 1H), 7.18-7.38 (m, 10H), 6.12 (d, 1H), 5.42 (dd, 1H), 5.05 (m, 2H), 3.40-4.40 (m, 7H), 2.55 (s, 3H), 1.36 (dd, 3H). LC-MS (ESI) 534 [M+]$^+$.

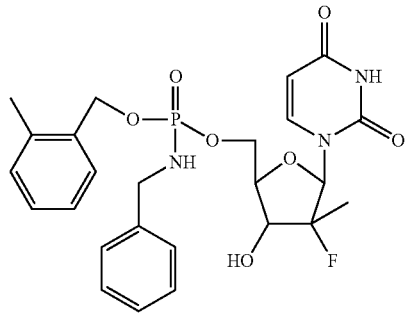

DGX-105

Example 5

DGX-106

δ$_H$ NMR, (CDCl$_3$): 8.91 (br. S, 1H), 7.15-7.36 (m, 11H), 6.11 (d, 1H), 5.43 (dd, 1H), 5.08 (m, 2H), 3.40-4.40 (m, 7H), 1.36 (dd, 3H). LC-MS (ESI) 520 [M+]$^+$.

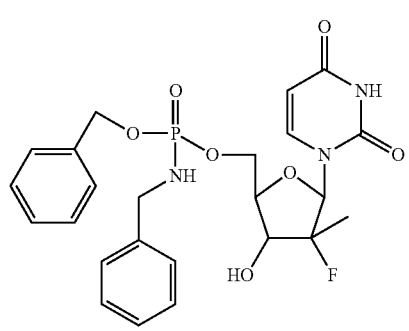

DGX-106

Example 6

DGX-108

δ$_H$ NMR, (CD$_3$OD): 7.57 (d, J=8.0 Hz, 1H), 7.24 (m, 9H), 6.10 (m, 1H), 5.73 (m, 1H), 5.00 (m, 2H), 4.26 (m, 2H), 4.01 (m, 4H), 2.32 (s, 3H). LC-MS (ESI) 559 [M+]$^+$.

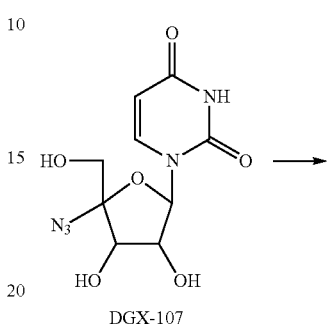

DGX-107

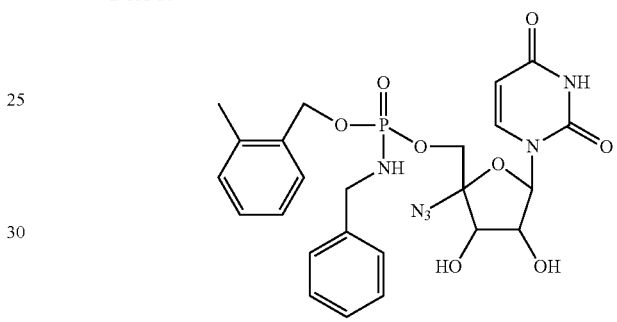

DGX-108

Example 7

Preparation of Compound DGX-110

To a mixture of 2'-C-methyl-2',3',5'-O-tribenzoyl-6-chloroguanosine (DGX-109, 3.13 g, 5 mmol) in MeOH (30 mL) was added a solution of NaOMe (4.8 M in MeOH, 5 mL, 24 mmol) and the resulting solution was stirred at room temperature for 16 h. Solvent was evaporated and the residue was purified by silica gel column chromatography (0-15% MeOH in CH$_2$Cl$_2$) to give DGX-110 (1.45 g, 93.5%) as white solid. δ$_H$ NMR, (DMSO-d$_6$): 8.19 (s, 1H), 6.47 (s, 2H), 5.80 (s, 1H), 5.21 (d, J=6.8 Hz, 1H), 5.14 (t, J=5.2 Hz, 1H), 5.08 (s, 1H), 3.94 (s, 3H), 3.98 (m, 1H), 3.80 (m, 2H), 3.65 (m, 1H), 0.77 (s, 3H). LC-MS (ESI) 312 [M+]$^+$.

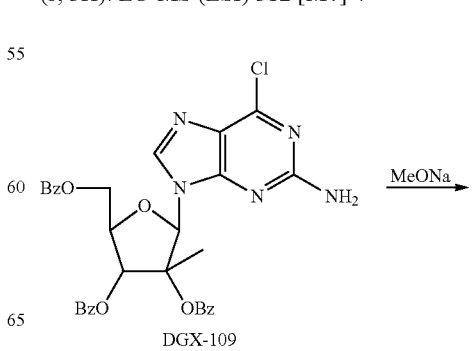

DGX-109

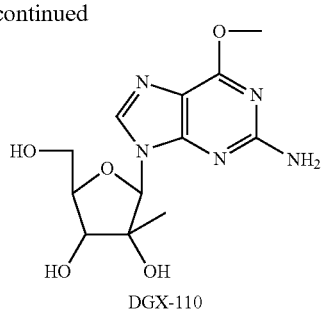

DGX-110

Example 8

DGX-111

According to above procedure for phosphoramidates, DGX-111 was prepared from DGX-110 as white foam. $\delta_H$ NMR, (CDCl$_3$): 7.80, 7.75 (ss, 1H, H-8), 7.20 (m, 10H, NH$_2$, Ph-H), 5.98 (ss, 1H, H-1'), 5.40 (ss, 2H, PhCH$_2$), 5.00 (m, 2H, PhCH$_2$N), 4.80-4.00 (10H, OCH$_3$, 20H, 3'-, 4'-, 5'-H), 2.25 (ss, 3H, Me), 0.95 (s, 3H, Me). LC-MS (ESI) 585 [M+]$^+$.

DGX-111

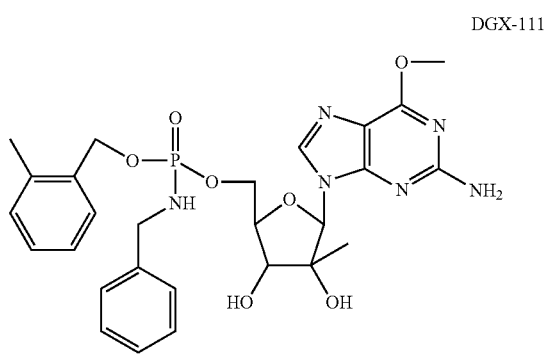 [SMILES: COc1nc(N)nc2c1ncn2C1OC(COP(=O)(NCc2ccccc2)OCc2ccccc2C)C(O)C1(C)O]

Example 9

According to above procedure, prodrugs of corresponding nucleosides in Table 1 and other prodrugs can be prepared. For example:

Gemzar Analog:

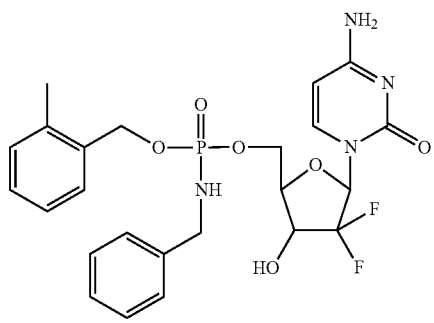

LC-MS (ESI) 537 [M+]$^+$

Fludarabine Analog:

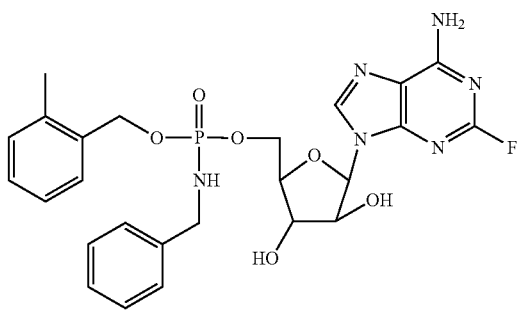

LC-MS (ESI) 559 [M+]$^+$

Vidaza (Azacitidine) Analog:

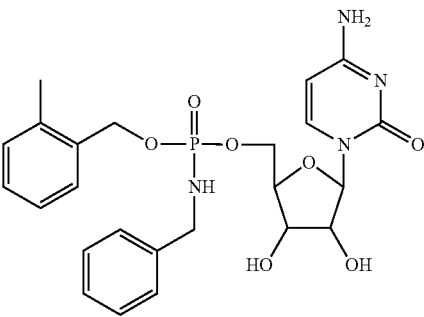

LC-MS (ESI) 517 [M+]$^+$

Example 10

Anticancer Assay (WO 2006/100439)

Compounds synthesized as anti-cancer agents can be each tested in leukaemic cell lines to assess their anticancer efficacy. The compounds can be tested using the MTS assay reagents from Promega (CellTiter96 Aqueous One solution proliferation assay). The compounds can be tested 5 µM (WO 2006/100439). Symbol, (+) indicates that the compound tested inhibits cellar growth greater than 50%.

Example 11

HCV Replicon Assay

The anti-HCV activity and toxicity of the exemplary compounds can be tested in two biological assays—a cell-based HCV replicon assay and cytotoxicity assay (WO 2007/027248).

I. Anti-HCV Assay

A human hepatoma cell line (Huh-7) containing replicating HCV subgenomic replicon with a luciferase reporter gene (luc-ubi-neo) was used to evaluate anti-HCV activity of the compounds. In this assay, level of luciferase signal correlates with the viral RNA replication directly. The HCV replicon-reporter cell line (NK/luc-ubi-neo) was cultured in DMEM medium supplemented with 10% fetal bovine serum and 0.5 mg/ml Geneticin (G418). Cells were maintained in a subconfluent state to ensure high levels of HCV replicon RNA synthesis.

To evaluate the antiviral activity of compounds, serial dilutions were prepared with concentrations ranging from 0.14 to 300 μM. Diluted compounds were transferred to a 96-well plate followed by the addition of replicon cells (6000 cells per well). Cells were incubated with the compounds for 48 h after which luciferase activity was measured. Reduction of luciferase signal reflected the decrease of HCV replicon RNA in the treated cells and used to determine the $EC_{50}$ value (concentration which yielded a 50% reduction in luciferase activity).

II. Cytotoxicity Assay

A Huh-7 cell line carrying a luciferase reporter gene (driven by a HIV LTR promoter) stably integrated into the chromosome was used to analyze the cytotoxic effect of the selected compounds. This cell line (LTR-luc) was maintained in DMEM medium with 10% FBS. Design of the cytotoxicity assay was similar to that of the HCV replicon assay. Reduction of luciferase activity in the treated cells correlated with the cytotoxic effect of the test compound and was used to calculate the $CC_{50}$ value (concentration that inhibited cell growth by 50%).

The biological activities using subgenomic genotype 1a replicon and cytotoxicity of the selected compounds are summarized in Table 2.

TABLE 2

Activity of exemplary compound in replicon assay

| Compd. | Replicon (μM) | $CC_{50}$ (μM) |
| --- | --- | --- |
| DGX-103 | >100 | >100 |
| DGX-104 | 4.1 | >100 |
| DGX-105 | 1.9 | >100 |
| DGX-106 | >100 | >100 |
| DGX-110 | 0.9 | >100 |
| DGX-111 | 0.3 | 69 |

The results of anti-HCV activity of the selected nucleosides and their prodrugs summarized in Table 2 indicated that prodrug technologies of the present invention can directly deliver nucleoside monophosphate into biological systems, such as cells and/or tissues. The prodrug technologies of the present invention can convert biologically inactive nucleoside, such as DGX-103, to a biologically potent nucleoside prodrug like DGX-104 and DGX-105. The prodrug technologies of the present invention can also convert biologically active nucleoside like DGX-110 to a biologically much more potent nucleoside prodrug, such as DGX-111.

It was discovered that substitution on the phenyl ring of benzyl ester dramatically changed biological property of the phosphoramidate of the present invention. For example, compounds DGX-104 and DGX-105 with 4-methoxy and 2-methyl substitution on phenyl ring demonstrated potent anti-HCV activity, respectively, while compound DGX-106 with unsubstituted benzyl group did not show any anti-HCV activity.

The prodrug technologies of the present invention can be applied to the most of nucleoside drugs to enhance their therapeutic potency or improve their biological properties.

Example 12

Anti-HBV Assay

Compounds of the present invention can be assayed for anti-HBV activity according to any assay known to those of skill in the art.

Example 13

Compounds can be assayed for accumulation in liver cells of a subject according to any assay known to those of skill in the art. In certain embodiments, a liver cell of the subject can be used to assay for the liver accumulation of compound or a derivative thereof, e.g. a nucleoside, nucleoside phosphate or nucleoside triphosphate derivative thereof.

Example 14

Pharmacokinetic (PK) study of prodrug FDURP (DGX-102) and parent drug (FDUR) in rats was completed according to following procedure.

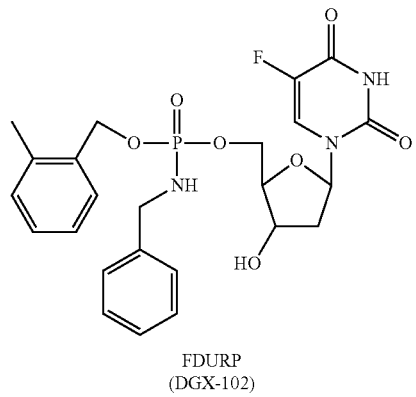

FDURP
(DGX-102)

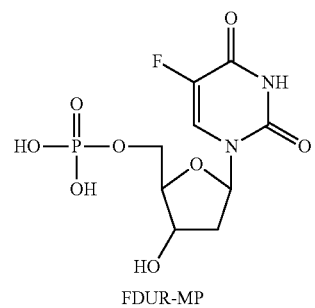

FDUR-MP

-continued

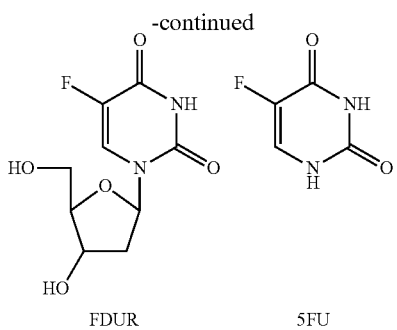

FDUR          5FU

SD rats (250-300 g, male, N=15) were used for each compound, purchased from SLAC Laboratory Animal Co. LTD Qualification No.: SCXK (SH) 2007-0005, 13264. Compounds FDUR and FDURP were each dosed via tail vein injection. The animal was restrained manually at designated time points. Approximately 500 µL of blood/time point was collected into $K_2$EDTA tube via cardiac puncture for terminal bleeding under anesthesia with Isoflurane. FDUR and FDURP blood samples were put on ice after collection and then centrifuged to obtain plasma sample (2000 g, 5 min, 4° C.) within 15 minutes of sampling. The blood samples were then centrifuged to obtain plasma sample (2000 g, 5 min, 4° C.). All the plasma samples were immediately quenched for protein precipitation. Liver samples of each compound were removed at designated time points by first sacrificing the animal by $CO_2$ inhalation, then perfusing the liver with ice cold saline and removing the left middle liver lobe, which was then snap frozen in dry ice. Liver samples were stored at approximately −80° C. until analysis. The liver homogenate was then processed for further analysis by LC/MS-MS. Plasma and liver samples were stored at approximately −80° C. until analysis.

Concentrations of prodrugs, parent drug and possible metabolites in both plasma and liver including FDURMP, FDUR, FDUR-MP and 5FU were determined by LC/MS-MS. The results were summarized in Table 3.

TABLE 3

Rat Plasma and Liver PK Profile after iv Administration of Compounds FDUR and FDURP

| Tested Compds | Monitored Compds | plasma | | | liver | | |
|---|---|---|---|---|---|---|---|
| | | Cmax (ng/mL) | Tmax (h) | AUC(inf) (ng · h/mL) | Cmax (ng/mL) | Tmax (h) | AUC(inf) (ng · h/mL) |
| FDUR | FDUR | 51.6 | NA | NA | BQL | NA | NA |
| | 5FU | 29.3 | 1 | NA | BQL | NA | NA |
| | FDUR-MP | BQL | NA | NA | BQL | NA | NA |
| FDURP | FDURP | | 0.45(T½) | 10400 | 1573 | 1 | 1750 |
| | FDUR | 39.7 | 1 | 41.4 | 49.8 | 8 | 838 |
| | 5FU | 14.2 | 1 | NA | 59.6 | 1 | NA |
| | FDUR-MP | BQL | NA | NA | 54.7 | 1 | NA |

TABLE 4

Rat Plasma and Liver PK Concentrations after iv Administration of Compounds FDUR and Prodrug FDURP

| | Drug FDUR Concentration (ng/mL) with FDUR (0.015 mmol/kg) | | Drug FDUR Concentration (ng/mL) with FDURP (0.015 mmol/kg) | |
|---|---|---|---|---|
| Sampling | Plasma | Liver | Plasma | Liver |
| 1 | 51.6 | BQL | 39.7 | BQL |
| 2 | BQL | BQL | 3.42 | BQL |
| 4 | BQL | BQL | BQL | 30.1 |
| 8 | BQL | BQL | BQL | 49.8 |
| 24 | BQL | BQL | BQL | 27.4 |

Exposures of prodrug FDURP both in plasma and in the liver were significantly greater than that for parent drug FDUR. The concentrations of the related active drugs including FDUR, FDUR-MP and 5FU after iv administration of FDURP were also significantly increased compared to that of administration of FDUR. The higher concentration of active metabolite, 5-fluoro-2'-deoxyuridine 5'-monophosphate (FDUR-MP) was detected in the liver after administration of FDURP but not from FDUR administration. These results indicated that prodrugs of the present invention can not only significantly enhance drug exposure and directly deliver active nucleotide into the liver, but also enrich the related active drugs in the liver.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims. All references cited hereby are incorporated by reference in their entirety.

What is claimed is:

1. A compound of formula I:

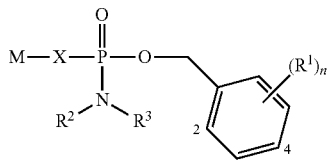

or a pharmaceutically acceptable salt, solvate, stereoisomer, tautomer, or prodrug thereof, wherein:
n is 1, 2, 3, 4, or 5;
X is oxygen (O) or —CH$_2$—;
M is a nucleoside, acyclonucleoside, C-nucleoside, or alcohol-containing drug molecule moiety;
$R^1$ at each occurrence is independently selected from acyloxy, acyl-NH—, alkyl, alkyloxyl, alkylamino, cycloalkyl, cycloalkyloxy, cycloalkylamino, aryl, aryloxy, arylamino, and arylalkyl, all optionally substituted; and
$R^2$ and $R^3$ are independently selected from H, alkyl, aryl, alkynyl, alkenyl, cycloalkyl, heterocyclyl and heteroaryl, all optionally substituted, wherein the heterocyclyl and heteroaryl each comprise one to three heteroatoms independently selected from O, S, and N, or alternatively,
$R^2$ and $R^3$ together, along with the N-atom to which they are attached, form an optionally substituted 4- to 7-membered ring.

2. The compound of claim 1, wherein at least one $R^1$ is attached to the 2- or 4-position of the phenyl ring in formula I.

3. The compound of claim 1, wherein $R^2$ and $R^3$ together are —(CH$_2$)$_i$—, wherein i is 3, 4, or 5.

4. The compound of claim 1, wherein $R^2$ and $R^3$ together, along with the N-atom to which they are attached, form a pyrrolidinyl group.

5. The compound of claim 1, characterized by formula II:

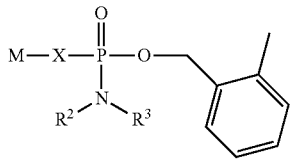

or a pharmaceutically acceptable prodrug, salt, or solvate thereof.

6. The compound of claim 1, characterized by formula III:

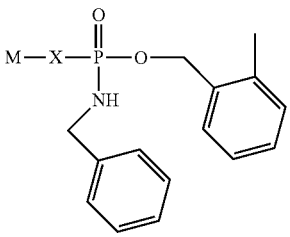

or a pharmaceutically acceptable prodrug, salt, or solvate thereof.

7. The compound of claim 1, characterized by formula IIIa or IIIb:

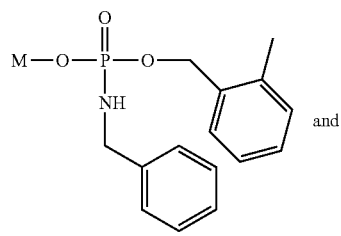

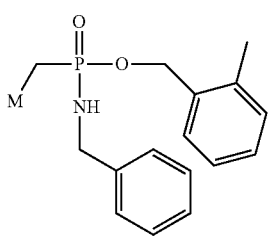

or a pharmaceutically acceptable prodrug, salt, or solvate thereof.

8. The compound of claim 1, wherein M is a nucleoside moiety comprising a sugar group and a base group.

9. The compound of claim 8, wherein the sugar group is substituted or unsubstituted ribose or 2-deoxyribose, and wherein the base group is selected from substituted or unsubstituted purines and substituted or unsubstituted pyrimidines.

10. The compound of claim 8, wherein the base group is selected from adenine, guanine, uracil, thymine, cytosine, and derivatives thereof.

11. The compound of claim 1, wherein X is O, and M is a structure of formula IV:

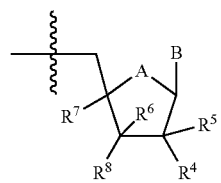

or pharmaceutically acceptable salt, solvate or prodrug thereof, wherein:
A is selected from O, S, CH$_2$, CHF, C=CH$_2$, C=CHF, and CF$_2$;
$R^4$ and $R^5$ are independently selected from H, OH, CH$_3$O, F, Cl, Br, I, CN, N$_3$, methyl, ethyl, vinyl, ethynyl, chlorovinyl, fluoromethyl, difluoromethyl, and trifluoromethyl, all optionally substituted, or alternatively
$R^4$ and $R^5$ together form a vinyl group optionally substituted with one or two groups independently selected from F, Cl, Br, I, CN, and N$_3$;
$R^6$ is selected from H, methyl, ethyl, vinyl, ethynyl, chlorovinyl, fluoromethyl, difluoromethyl, and trifluoromethyl;
$R^7$ is selected from H, CN, N$_3$, methyl, ethyl, vinyl, ethynyl, chlorovinyl, fluoromethyl, difluoromethyl, and trifluoromethyl;

$R^8$ is selected from H, OH, F, cyano, and azido; and

B is a pyrimidine or purine base selected from formulae B-1 and B-2:

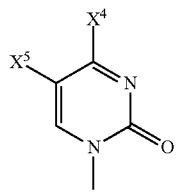

B-1

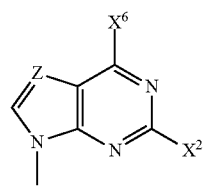

B-2 wherein:

X² is selected from H, NH₂, NHMe, NMe₂, and halogen (I, Br, Cl, F), all optionally substituted;

X⁴ is NH₂ or OH;

X⁵ is selected from halogen (I, Br, Cl, F), OH, NH₂, methyl, vinyl, alkyl, 2-bromovinyl, and ethynyl, all optionally substituted;

X⁶ is selected from H, OH, OMe, OEt, SMe, alkyloxy, aryloxy, cycloalkyloxy, alkylthio, arylthio, cycloalkylthio, thienyl, furyl, alkylamino, dialkylamino, arylamino, arylalkylamino, cycloalkylamino, and cyclopropylamino, all optionally substituted;

Z is nitrogen (N) or CX⁷; and

X⁷ is selected from H, vinyl, ethynyl, and halogen (I, Br, Cl, F), all optionally substituted;

wherein any said amino and hydroxyl groups are optionally protected by a group hydrolysable under physiological conditions in vivo.

12. The compound of claim 1, wherein M is an acyclic nucleoside moiety selected from acyclovir, gancyclovir, pencyclovir, C-nucleosides, and prodrugs thereof.

13. The compound of claim 1, having a formula:

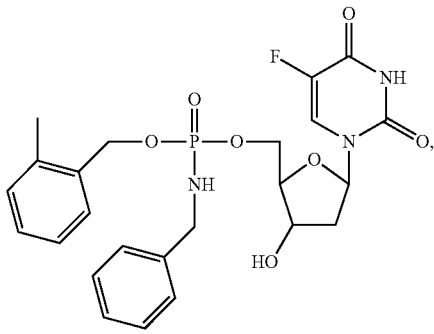

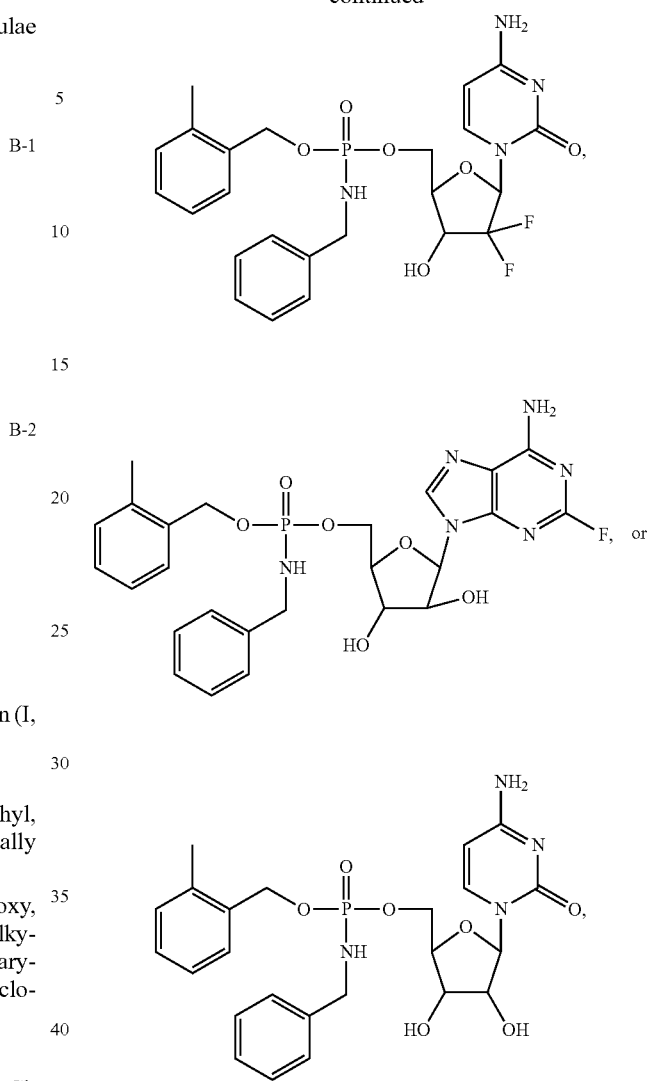

or a pharmaceutically acceptable salt, solvate, or prodrug thereof.

14. A pharmaceutical composition comprising a compound of claim 1, and a pharmaceutically acceptable carrier or diluent.

15. A method of treating a viral infection or cancer, wherein the viral infection or cancer is selected from hepatitis B infection, hepatitis C infection, and liver cancer, comprising administration of a compound of claim 1, or a pharmaceutically acceptable prodrug thereof, to a patient in need of the treatment.

16. The method of claim 15, wherein said compound is a prodrug of nucleoside, acyclic nucleoside, C-nucleoside, nucleotide, or other alcohol-containing drug molecule.

17. The method of claim 16, in combination with administration of a second or more therapeutically active drug(s).

18. A method of treating a viral infection or cancer, wherein the viral infection or cancer is selected from hepatitis B infection, hepatitis C infection, and liver cancer, comprising administration of a pharmaceutical composition according to claim 14 to a patient in need of the treatment.

19. The compound of claim 8, wherein said nucleoside is selected from the group consisting of:
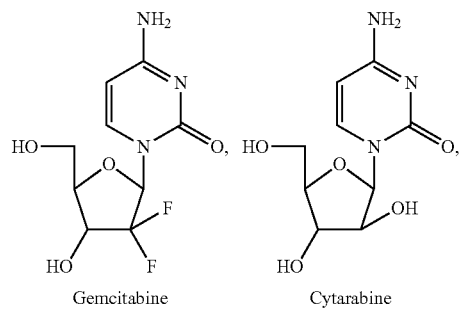
Gemcitabine, Cytarabine
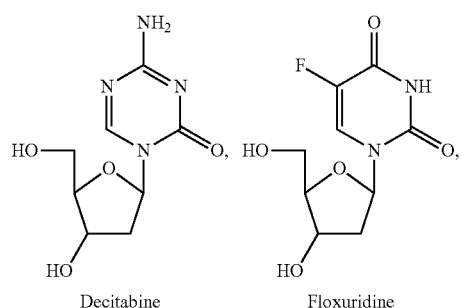
Decitabine, Floxuridine
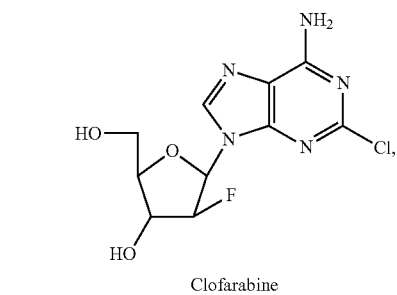
Clofarabine
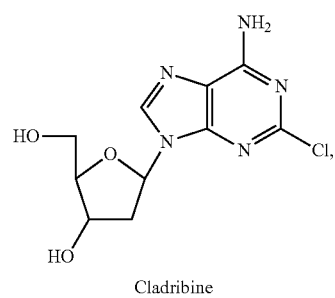
Cladribine
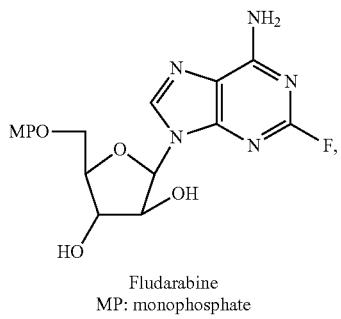
Fludarabine
MP: monophosphate
-continued
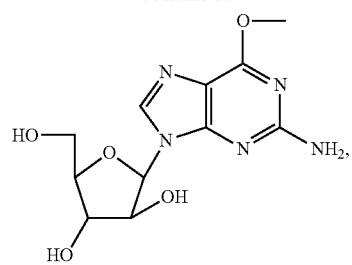
Nelarabine
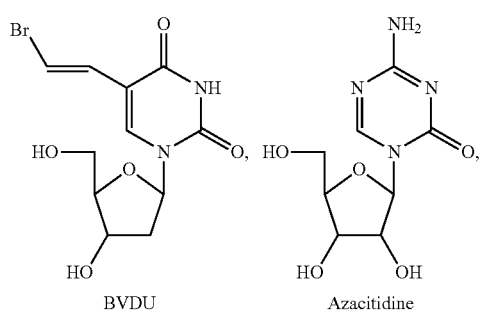
BVDU, Azacitidine
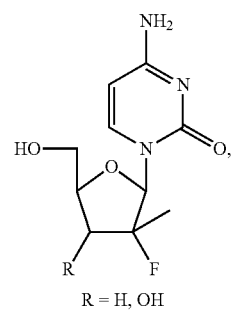
R = H, OH
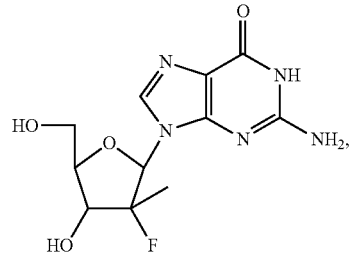
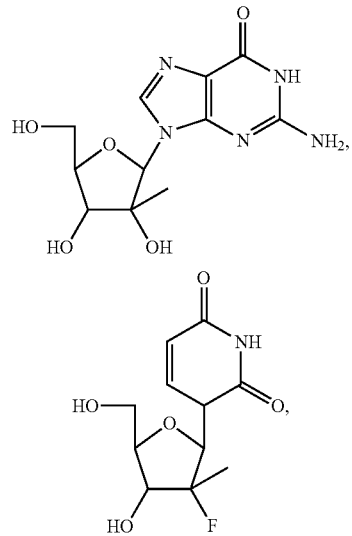

-continued
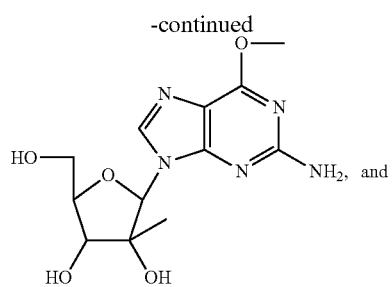
and
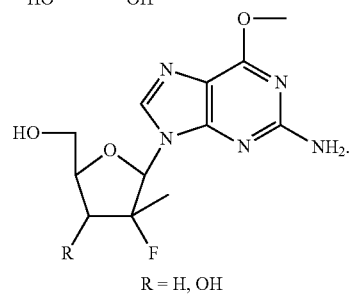
R = H, OH
* * * * *